(12) United States Patent
Duramad et al.

(10) Patent No.: US 9,821,035 B2
(45) Date of Patent: Nov. 21, 2017

(54) PREPARATION FOR PREVENTING OR TREATING TYPE I DIABETES

(71) Applicant: REGIMMUNE CORPORATION, Chuo-ku (JP)

(72) Inventors: Omar Duramad, Berkeley, CA (US); Hidetoshi Akimoto, Chuo-ku (JP); Yasuyuki Ishii, Chuo-ku (JP); Haruhiko Morita, Chuo-ku (JP)

(73) Assignee: REGIMMUNE CORPORATION, Chuo-ku (JP)

( * ) Notice: Subject to any disclaimer, the term of this patent is extended or adjusted under 35 U.S.C. 154(b) by 76 days.

(21) Appl. No.: 14/422,989

(22) PCT Filed: Aug. 22, 2013

(86) PCT No.: PCT/JP2013/072441
§ 371 (c)(1),
(2) Date: Feb. 20, 2015

(87) PCT Pub. No.: WO2014/030708
PCT Pub. Date: Feb. 27, 2014

(65) Prior Publication Data
US 2015/0238572 A1 Aug. 27, 2015

Related U.S. Application Data

(60) Provisional application No. 61/692,084, filed on Aug. 22, 2012.

(51) Int. Cl.
| | | |
|---|---|---|
| *A61K 38/28* | (2006.01) | |
| *A61K 31/7032* | (2006.01) | |
| *C07K 14/62* | (2006.01) | |
| *A61K 9/127* | (2006.01) | |
| *A61K 39/00* | (2006.01) | |

(52) U.S. Cl.
CPC ............ *A61K 38/28* (2013.01); *A61K 9/127* (2013.01); *A61K 31/7032* (2013.01); *C07K 14/62* (2013.01); *A61K 2039/55555* (2013.01)

(58) Field of Classification Search
None
See application file for complete search history.

(56) References Cited

U.S. PATENT DOCUMENTS

| | | | |
|---|---|---|---|
| 2004/0022840 A1* | 2/2004 | Nagy | A61K 9/1273 424/450 |
| 2007/0104776 A1 | 5/2007 | Ishii et al. | |
| 2012/0121688 A1 | 5/2012 | Ishii et al. | |

FOREIGN PATENT DOCUMENTS

| | | |
|---|---|---|
| WO | 94/23737 A1 | 10/1994 |
| WO | 01/54700 A1 | 8/2001 |
| WO | 2005 120574 | 12/2005 |
| WO | 2007 080977 | 7/2007 |

OTHER PUBLICATIONS

Alleva et al., "Immunological Characterization and Therapeutic Activity of an Altered-Peptide Ligand, NBI-6024, Based on the Immunodominant Type 1 Diabetes Autoantigen Insulin B-Chain (9-23) Peptide" Diabetes (2002) vol. 51 No. 7 pp. 2126-2134.*
Achenbach, "Modulating the Natural History of Type 1 Diabetes in Children at High Genetic Risk by Mucosal Insulin Immunization" Current Diabetes Reports (2008) vol. 8 pp. 87-93.*
Sharif et al., "Activation of natural killer T cells by alpha-galactosylceramide treatment prevents the onset and recurrence of autoimmune Type 1 diabetes" Nature (2001) vol. 7 No. 9 pp. 1057-1062.*
Wang, B. et al., "Parameters influencing antigen-specific immunotherapy for type 1 diabetes", Immunologic Research, vol. 41, No. 3, (2008), pp. 175-187.
Li, W. et al., "Cooperation of invariant NKT cells and $CD4^+CD25^+$ T regulatory cells in prevention of autoimmune diabetes in non-obese diabetic mice treated with α-galactosylceramide", Acta Biochimica Et Biophysica Sinica, vol. 40, No. 5, (2008), pp. 381-390.
Tamura, Y. et al., "Characterization of the immature dendritic cells and cytotoxic cells both expanded after activation of invariant NKT cells with α-galactosylceramide in vivo", Biochemical and Biophysical Research Communications, vol. 369, No. 2, (2008), pp. 485-492.
Ishii, Y., "Regulatory mechanisms for attenuation of allergic responses by iNKT cells", Clinical Immunology & Allergology, vol. 55, No. 3, (2011), pp. 289-293.
Stein, C., et al., "Treatment of spinal cord-induced experimental allergic encephalomyelitis in the Lewis rat with liposomes presenting central nervous system antigens", Journal of Neuroimmunology, vol. 28, No. 2, (1990), pp. 119-130.
International Search Report dated Oct. 15, 2013 in PCT/JP13/072441 Filed Aug. 22, 2013.
European Search Report issued for Counterpart European Patent Application No. 13831340.8 dated Mar. 2, 2016.
Maki Nakayama, et al., "Insulin as a key autoantigen in the development of type 1 diabetes", Diabetes/Metabolism Research and Reviews 2011; 27: pp. 773-777.
Li Zhang et al., "Insulin as an autoantigen in NOD/human diabetes", Current Opinion in Immunology 2008, 20: pp. 111-118.
Claire Forestier, et al., "Improved Outcomes in NOD Mice Treated with a Novel Th2 Cytokine-Biasing NKT Cell Activator", The Journal of Immunology 2007; 178: pp. 1415-1425.
Jason Ken-Shun Hung, "Liposomal Alpha-Galactosylceramide Plus Insulin Effects on Type 1 Diabetes in Non-Obese Diabetic Mice", The University of British Columbia (Vancouver), Apr. 2014.

* cited by examiner

*Primary Examiner* — Eric S Olson
(74) *Attorney, Agent, or Firm* — Oblon, McClelland, Maier & Neustadt, L.L.P.

(57) ABSTRACT

The purpose of the present invention is to provide a preparation for preventing or treating type I diabetes, said preparation exerting an excellent effect of preventing or treating type I diabetes, and a method for preventing or treating type I diabetes. The onset and symptoms of type I diabetes can be very remarkably relieved by dosing a combination of: (A) at least one member selected from the group consisting of proinsulin, insulin, insulin A chain, insulin B chain, fragments thereof and variants thereof; with (B) α-GalCer.

8 Claims, 5 Drawing Sheets

SEQUENCE LISTING

<160> NUMBER OF SEQ ID NOS: 4

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 15
<212> TYPE: PRT
<213> ORGANISM: Homo sapiens

<400> SEQUENCE: 3

Ser His Leu Val Glu Ala Leu Tyr Leu Val Cys Gly Glu Arg Gly

```
1               5               10              15

<210> SEQ ID NO 4
<211> LENGTH: 17
<212> TYPE: PRT
<213> ORGANISM: Homo sapiens

<400> SEQUENCE: 4

Leu Val Glu Ala Leu Tyr Leu Val Cys Gly Glu Arg Gly Phe Phe Tyr
1               5                   10                  15

Thr
```

PREPARATION FOR PREVENTING OR TREATING TYPE I DIABETES

TECHNICAL FIELD

The present invention relates to a preparation for preventing or treating type I diabetes, and to a method for preventing or treating type I diabetes.

BACKGROUND ART

Type I diabetes, which is an autoimmune disease, is caused by the destruction of pancreatic β cells resulting from abnormal function of the autoimmune system. Pancreatic β cells are a subset of cells composing the islets of Langerhans (pancreatic islets) located in the interstitial tissue of the pancreas, and produce insulin, which is crucial for the maintenance of life, and are involved in the regulation of the in vivo metabolism, for example, of glucose metabolism, protein synthesis, formation and storage of neutral fat, and the like. The destruction of pancreatic β cells causes the lack of insulin in the living body, resulting in abnormalities in glucose tolerance, such as disordered sugar metabolism, whereby blood glucose levels are not maintained in a normal range, and in severe cases, leading to crises of life, such as chronic hyperglycemia, glycosuria, loss of water and electrolytes, ketoacidosis, and coma. In addition, complications for long periods include, for example, neurological disorders, retinopathies, renal disorders, systemic degenerative changes of large or small blood vessels, and infections.

At the present time, the most common and practical therapeutic method for type I diabetes is one by which a pharmaceutical containing insulin or a modified insulin as a main ingredient is administered twice or more per day. Patients who have developed type I diabetes have to continue such a therapeutic method for the rest of their lives and must always have the pharmaceutical at hand, which can be said to be a therapeutic method with extremely poor compliance.

With respect to the mechanism of its development, it is widely recognized from many research reports that based on abnormal function of the suppressive immune system, the development of type I diabetes closely correlates with the activation of CD4-positive T cells and CD8-positive T cells specific for self-antigens derived from the pancreatic islets. In addition to genetic predispositions, infection with certain viruses and exposure to environmental factors such as diet trigger a decrease in the number of and abnormal function of regulatory T cells (Treg cells) and natural killer T cells (NKT cells) responsible for antigen-specific immunosuppression. Such abnormal function of the suppressive immune system activates self-antigen-reactive type 1 helper T cells (pathogenic Th1 cells, which are CD4-positive cells), which would normally be subjected to suppression, and further activates self-antigen-specific cytotoxic T cells (CTLs, which are CD8-positive cells), resulting in specific destruction of the pancreatic β cells by CTLs invaded in the pancreatic islets, which causes their irreversible dysfunction.

A number of studies have been made and reported on the basis of the idea that based on the recognition as described above, the induction of the suppressive immune system to self-antigens derived from the pancreatic islets and the suppression of the production of pathogenic Th1 cells and self-antigen-specific CTLs lead to an improvement in the effect of prevention of the onset of type I diabetes and of treatment of type I diabetes.

For example, studies which are intended to improve the effect of prevention of the onset of type I diabetes and of treatment of type I diabetes by returning suppressive immune functions to normal are directed to the induction of self-antigen-specific Treg cells. According to these studies, self-antigen-specific Treg cells are induced by immunization with a certain self-antigen alone or in combination with an adjuvant. The induced Treg cells are then activated in the pancreas or pancreatic lymph nodes expressing the self-antigen, so that the activation of pathogenic Th1 cells is suppressed, while the cytotoxic activity of CTLs which infiltrate in the pancreatic islets and destroy pancreatic β cells is suppressed by by-stander effects. Non-Patent Documents 1 and 3 report that in tests in pre-diabetic NOD mice, insulin and an insulin peptide B:9-23, which are self-antigens, exhibited effects of delaying the progress of diabetes and suppressing its onset when the NOD mice were immunized with these self-antigens. In addition, Patent Document 1 reports that the onset of type I diabetes can be suppressed by administration of the B chain of insulin or a fragment thereof and an adjuvant for enhancing immune responses. Although, as reported, antigen-specific immunosuppression was shown to be effective in preventing the onset of type I diabetes and treating type I diabetes, drugs exerting a satisfactory effect or their clinical application have not been established.

Further, studies which are intended to improve the effect of prevention of the onset of type I diabetes and of treatment of type I diabetes by returning other suppressive immune functions to normal are directed to attempting to accomplish a qualitative and functional improvement of NKT cells. From these studies, it has been known that such an improvement has an effect of delaying the onset of the disease. NKT cells secrete interleukin 4 (IL-4) and IL-10, which are cytokines, whereby they suppress unnecessary activation and abnormal immune responses of other immune cells, so that they regulate functions of the entire immune system to be maintained at normal levels. Pre-diabetes groups with genetic predispositions have been observed to have smaller numbers of NKT cells and reduced amounts of IL-4 production, and it has been suggested that NKT cells may be involved in the onset of diabetes. In this regard, research was made on the prevention of the onset of diabetes by the activation of NKT cells through the administration of a glycolipid, α-galactosylceramide (α-GalCer), which is a ligand of NKT cells. For example, Patent Document 2 indicates that the administration of α-GalCer delays the onset of type I diabetes. However, the administration of α-GalCer exhibited an effect of delaying the onset of the disease, but did not provide a sufficient preventive effect against the disease (see Patent Document 2, and Examples 2 and 3 described below), and thus has not lead to clinical application. Furthermore, Patent Document 2 discloses an example in which α-GalCer was administered into the thymus, but examinations were not performed on what effect the difference in the mode of administration of α-GalCer has on the effect of prevention or treatment of type I diabetes.

These methods in which the onset of type I diabetes is suppressed by administration of insulin or an insulin peptide alone or of α-GalCer alone require continuous administration of these respective agents, and thus do not provide a solution to the problem of frequent administration, which is an obstacle to current treatments with insulin and modified insulin.

On the other hand, it has been proposed to use α-GalCer to prevent the onset of or to treat allergic diseases caused by the production of certain antibodies, as well as autoimmune diseases of the type in which the production of an antibody (autoantibody) is greatly related to the onset of the disease. For example, Patent Document 3 reports that immune diseases such as allergic diseases can be prevented or treated by administration of liposomes containing α-GalCer, whereby the drug is transported into immune cells in the spleen where antibodies are produced, so that the effects of inducing T cells producing IL-10 and of suppressing the production of IgE antibodies are exhibited in a spleen-specific manner. Patent Document 4 reports that autoimmune diseases such as systemic lupus erythematosus (SLE) and rheumatism can be prevented or treated with preparations having α-GalCer and a target antigen contained in a liposome, allowing the drug to be transported into immune cells in the spleen, thereby providing an effect of suppressing the production of IgE antibodies resulting from the target antigen and, at the same time, an effect of suppressing the production of autoantibodies resulting from the target antigen. These methods in which α-GalCer is used to prevent or treat autoimmune diseases are expected to be effective for preventing the onset of or treating SLE and rheumatism by virtue of the effect of suppressing the production of antigen-specific autoantibodies. However, in cases of autoimmune diseases of the type in which suppressive immune functions are attenuated as in type I diabetes and the destruction of pancreatic islets due to the activation of pathogenic Th1 cells and self-antigen-specific CTLs resulting from self-antigens or epitopes is greatly associated with the onset of the disease, the suppression of the production of antibodies is generally thought to have no relevance to techniques that improve the effect of prevention or treatment of diabetes (Non-Patent Documents 1 and 2).

As described above, it is important, in preventing the onset of type I diabetes or improving the effect of treatment of type I diabetes, to improve the function of the self-antigen-specific suppressive immune system, and to suppress the activation of pathogenic Th1 cells and to suppress the production of self-antigen-specific CTLs. When such antigen-specific immunotherapies are carried out, the ascertainment of self-antigens or epitopes is very important in improving therapeutic effects. Epitopes stemming from proteins derived from the pancreatic islets have been found in association with type I diabetes: for example, examinations of antibodies in the serum from patients with type I diabetes revealed the production of antibodies directed to three proteins derived from the pancreatic islets, insulin, glutamic acid decarboxylase (GAD65), and islet tyrosine phosphatase (IA-2), and further, search studies for T-cell epitopes found islet-specific glucose-6-phosphatase catalytic subunit-related protein (IGRP), zinc transporter (ZnT8), and others. Among these, insulin-derived antigens are expected to be a major factor in the onset of type I diabetes, and it has also been found that about 80% of the CD8-positive T-cell epitopes derived from human pancreatic β cells that have been found in the past are derived from proinsulin and insulin (Non-Patent Document 3). For major T-cell epitopes from proinsulin/insulin, a peptide "B:9-23," which is composed of amino acids 9 to 23 of the B chain in the insulin molecule, was identified in NOD mice (Non-Patent Document 4), and a peptide "B:11-27," which is composed of amino acids 11 to 27 of the B chain in the insulin molecule was identified in humans (Non-Patent Document 5). In tests using non-obese diabetic (NOD) mouse, which is an animal model for type I diabetes, the deficiency of GAD65 or IA-2 did not suppress the onset of the disease, whereas the deficiency of insulin B:9-23 resulted in complete suppression of its onset. Also from these results, it is suspected that proinsulin-derived epitopes may be deeply involved in the onset of type I diabetes.

In addition, cell/tissue transplantation therapies in which a normal pancreatic islet tissue is transplanted to patients with diabetes are also known as an effective therapy for diabetes. These transplantation therapies are considered to be very effective especially for patients who have difficulty in controlling the level of blood sugar and who are of a type in which the insulin treatment and diet and exercise therapy are not effective and severe hypoglycemic episodes are caused. However, at the same time, there are several problems, for example, in that it is difficult at this time to maintain control of blood sugar levels for an extended period by a single transplantation and thus more than one transplantations have to be performed. For example, Non-Patent Document 6, which is an article written by a group of Edmond A. Ryan et al. in Edmonton, Canada, reports the results of five-year follow-up after islet transplantation, showing that 50 to 70% of the transplants were lost at relatively early stages after the transplantation. This would be attributed to body's responses to the transplant. For example, it is thought that the transplants were injured and lost by activation of the blood coagulation cascade and the complement system, such as platelet aggregation, non-specific inflammatory responses by macrophages, and innate immune responses. Additionally, islet transplants that have escaped from injury at early stages after the transplantation will be damaged by self-antigen-specific CTLs present prior to transplantation in the patients and subjected to progressive damage to the pancreatic islets, making it difficult to maintain long-term control of blood sugar levels. In order to overcome problems in these transplantation therapies and to improve the effect of treatment, it is important to use an anti-inflammatory agent and to develop a new immunosuppressive therapy targeting self-antigen-specific CTLs.

Taking these conventional techniques into consideration as a background, there is a strong need for development of a preparation which is remarkably excellent in the effect of prevention or treatment of type I diabetes and is clinically applicable.

PRIOR ART DOCUMENTS

Non-Patent Documents

Non-Patent Document 1: Devasenan D. et al., BMJ, 2004, 328, 750-754

Non-Patent Document 2: Stephan M. et al., N. Engl. J. Med., 2001, 345, 1036-1040

Non-Patent Document 3: T. P. Di Lorenzo et al., Clinical and Experimental Immunology, 148:1-16

Non-Patent Document 4: Daniel D. et al., PNAS, 1996, 93, 956-960

Non-Patent Document 5: Schloot N C. et al., JAI, 1998, 11, 169-175

Non-Patent Document 6: Edmond A. Ryan et al., Diabetes, vol. 54, 2005, 2060-69

Non-Patent Document 7: Filippi C. et al., Inter. Reviews. Immun., 2005, 24, 341-360

Patent Documents

Patent Document 1: WO 94/23737
Patent Document 2: WO 99/33475
Patent Document 3: WO 2005/120574
Patent Document 4: WO 2007/80977

SUMMARY OF THE INVENTION

Problems to be Solved by the Invention

The present invention is aimed at providing a preparation and a method for preventing or treating type I diabetes, the preparation and the method exerting an excellent effect for the prevention or treatment of type I diabetes.

Means for Solving the Problems

The inventors made an extensive study to solve the above-described problems, and as a result, found that it is possible to suppress the onset and symptoms of type I diabetes to an especially remarkable extent by administrating a combination of (A) at least one member selected from the group consisting of proinsulin, insulin, insulin A chain, insulin B chain, a fragment thereof and a variant thereof; and (B) α-GalCer. The present invention has been completed through further examinations on the basis of this finding.

That is, the present invention provides agents and methods for prevention or treatment whose aspects are described below.

Item 1. A preparation for prevention or treatment of type I diabetes, comprising (A) at least one member selected from the group consisting of proinsulin, insulin, insulin A chain, insulin B chain, fragments thereof and variants thereof, and (B) α-galactosylceramide.

Item 2. The preparation according to item 1, wherein the component (A) is at least one member selected from the group consisting of proinsulin, insulin B chain, fragments thereof and variants thereof.

Item 3. The preparation according to item 1 or 2, wherein the component (B) is KRN7000.

Item 4. The preparation according to any one of items 1 to 3, wherein the component (B) is contained in a liposome.

Item 5. The preparation according to any one of items 1 to 4, wherein the component (A) and the component (B) are contained in a liposome.

Item 6. The preparation according to any one of items 1 to 5, wherein the preparation is used for the prevention of type I diabetes.

Item 7. The preparation according to any one of items 1 to 6, wherein the preparation is administered in the form of subcutaneous or intraperitoneal administration.

Item 8. A method for prevention or treatment of type I diabetes, comprising
administering a therapeutically or prophylactically effective amount of a preparation to a human in need of prevention or treatment of type I diabetes,
wherein the preparation comprises (A) at least one member selected from the group consisting of proinsulin, insulin A chain, insulin B chain, fragments thereof and variants thereof, and (B) α-galactosylceramide.

Item 9. The method for prevention or treatment according to item 8, wherein the component (A) is at least one member selected from the group consisting of proinsulin, insulin B chain, fragments thereof and variants thereof.

Item 10. The method for prevention or treatment according to item 8 or 9, wherein the component (B) is KRN7000.

Item 11. The method for prevention or treatment according to any one of items 8 to 10, wherein the component (B) is contained in a liposome.

Item 12. The method for prevention or treatment according to any one of items 8 to 11, wherein the component (A) and the component (B) are contained in a liposome.

Item 13. The method for prevention or treatment according to any one of items 8 to 12, wherein the human is a human in need of the prevention of type I diabetes.

Item 14. The method for prevention or treatment according to any one of items 8 to 13, wherein the preparation is administered in the form of subcutaneous or intraperitoneal administration.

Item 15. Use of a preparation comprising (A) at least one member selected from the group consisting of proinsulin, insulin, insulin A chain, insulin B chain, fragments thereof and variants thereof, and (B) α-galactosylceramide, for the manufacture of an agent for the prevention or treatment of type I diabetes.

Advantages of the Invention

Type I diabetes cannot be prevented from occurring or treated with a sufficient effect by administration of either of at least one member selected from the group consisting of proinsulin, insulin, insulin A chain, insulin B chain, fragments thereof and variants thereof, or α-GalCer alone. According to the present invention, however, it is possible to achieve effective suppression of the onset of type I diabetes or effective treatment of type I diabetes by administrating them in combination. The suppression of the onset of type I diabetes or treatment of type I diabetes according to the present invention is realized by suppressing the activation of self-antigen-specific pathogenic Th1 cells and by suppressing the induction of CTLs specifically attacking pancreatic β cells, and thus is based on a mechanism that is unpredictable by analogy from the previously reported action of α-GalCer, because the present invention uses a mechanism different from the previously reported mechanism by which the production of allergen-specific antibodies and autoantibodies is inhibited using α-GalCer. According to the mechanism by the present invention, the onset of type I diabetes can be significantly suppressed by subcutaneous or intraperitoneal administration rather than by intravenous administration.

In particular, it is possible in the present invention to achieve suppression of the onset of type I diabetes or radical treatment of type I diabetes that is further more effective and has less side-effects since the above-described one component is used in combination with α-GalCer, in which the one component is incorporated in a liposome containing the α-GalCer, whereby cells such as plasmacytoid dendritic cells (pDCs) are induced and allowed to gather into the pancreatic lymph nodes so that a subset of suppressive T cells involved in the treatment is induced and allowed to gather in a pancreas-specific manner, and whereby pathogenic Th1 cells and CTLs are effectively suppressed and allowed to be lost so that the destruction of the pancreas is blocked, while the drug is selectively transported to the target cells, making it possible to reduce the amount of the drug used.

Furthermore, in cases where type I diabetes is to be treated by transplantation of β cells, allogeneic pancreatic islets have been previously used as the source of β cells. As the procedure for transplantation, a method referred to as the Edmonton Protocol has mainly been employed in which large amounts of β cells are implanted. However, major problems associated with this type of transplantation are principally that the supply of allogeneic pancreatic islets is overwhelmingly short to meet the demand of β cells and that the implanted β cells are destroyed after the transplantation by autoimmunity causing the original disease. The problem regarding the supply of β cells can be solved by means of β cells derived from iPS or ES cells, whereas it can be said that there is still not a method to solve the problem that the implanted β cells are destroyed, and thus it is the current situation that alternative methods are employed in which the implanted cells are protected from autoimmunity by, for example, encapsulation of the cells to be implanted. According to the present invention, however, it is possible, by using an α-GalCer-containing liposome having the above-described one component incorporated therein, to suppress autoimmunity directed to the transplant of β cells so that extremely effective suppression of the onset of type I diabetes is achieved also in conjunction with the transplantation of β cells.

EMBODIMENTS OF THE INVENTION

Figure 1:
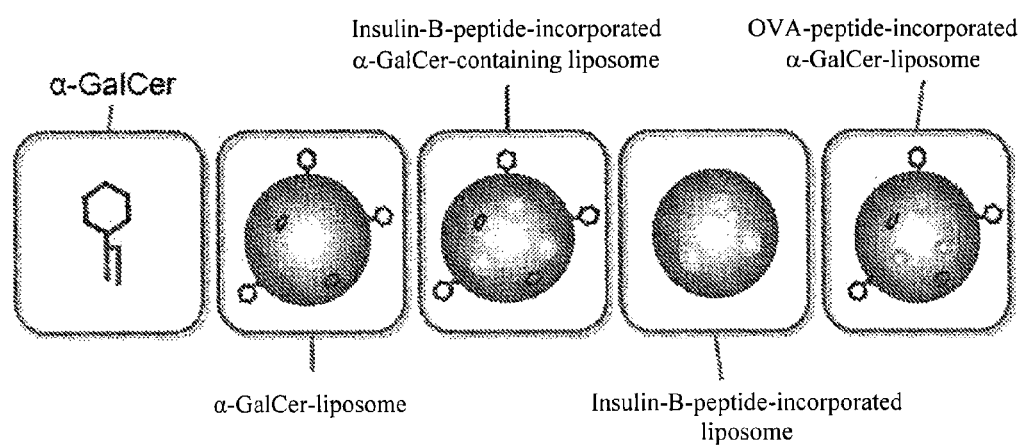
FIG. 1 represents schematic structures of samples for administration which were used in Examples 2 and 3.

A preparation of the present invention is a medicament which contains at least one member selected from the group consisting of proinsulin, insulin, insulin A chain, insulin B chain, a fragment thereof and a variant thereof (sometimes referred to hereinafter as a component (A)), and α-GalCer (sometimes referred to hereinafter as a component (B)) and which is used for the prevention or treatment of type I diabetes. The present invention is described below in detail.

Component (A)

A preparation of the present invention contains, as the component (A), at least one member selected from the group consisting of proinsulin, insulin, insulin A chain, insulin B chain, fragments thereof and variants thereof.

The preparation of the present invention is a medicament which is used for the prevention or treatment of type I diabetes. The component (A) is a molecule that acts as a target for accomplishing this purpose, and not only is insulin, but also can be other proteins derived from the pancreatic islets, such as GAD65 and IA-2, and in addition, IGRP, ZnT8, and others that were found in studies searching for T-cell epitopes. The inventors, however, have found that among these, proinsulin, insulin, insulin A chain, insulin B chain, fragments thereof and variants thereof are extremely useful as the component (A) and the effect of prevention or treatment of type I diabetes is achieved to a remarkable extent by incorporating them in α-GalCer-containing liposomes as described below.

Since the present invention relates to the prevention or treatment of human type I diabetes, it is desirable that the proinsulin, insulin, insulin A chain, insulin B chain, fragments thereof and variants thereof which are used as the component (A) are derived from humans.

Proinsulin is a precursor of insulin. Insulin is a peptide hormone having the structure in which C-peptide is released from proinsulin and the resulting A and B chains are bonded by two disulfide bonds. Insulin A chain is a peptide of 21 amino acid residues, and insulin B chain is a peptide of 30 amino acid residues. The amino acid sequences of proinsulin, insulin, insulin A chain, and insulin B chain are publicly known. For example, it is known that the amino acid sequence of human insulin A chain is GIVEQCCTSICSLY-QLENYCN (SEQ ID NO: 1) and the amino acid sequence of human insulin B chain is FVNQHLCGSHLVEALYL-VCGERGFFYTPKT (SEQ ID NO: 2).

Fragments of proinsulin, insulin, insulin A chain, and/or insulin B chain are not limited in particular, as long as they are capable of exhibiting a protective effect against type I diabetes. In the case of type I diabetes, among these fragments, insulin B-chain fragments including an amino acid sequence of amino acids 9 to 23 of the insulin B chain and insulin B-chain fragments including an amino acid sequence of amino acids 11 to 27 of the insulin B chain are suitable since it has been revealed that a peptide having an amino acid sequence consisting of amino acids 9 to 23 of the insulin B chain (B:9-23, amino acid sequence: SHLVEALYLVCGERG (SEQ ID NO: 3)) and a peptide having an amino acid sequence consisting of amino acids 11 to 27 of the insulin B chain (B:11-27, amino acid sequence: LVEALYLVCGERGFFYT (SEQ ID NO: 4)) are major antigen epitopes of CD4$^+$ T cells.

Variants of proinsulin, insulin, insulin A chain, insulin B chain, and/or fragments thereof are ones having an amino acid sequence in which one or more amino acids are substituted in, deleted from, and/or added to the parent amino acid sequence of the variant. In such a variant, the number of amino acid mutations is not limited in particular, as long as the variant is capable of exhibiting a protective effect against type I diabetes. For example, in cases of variants of proinsulin or insulin, examples of these variants include ones having an amino acid sequence in which one to several amino acids, preferably one to five amino acids, and further preferably one to two amino acids are substituted in, deleted from, and/or added to the amino acid sequence constituting each of the insulin A and B chains. In cases of variants of insulin B chain or fragments thereof, examples of these variants include ones having an amino acid sequence in which one to several amino acids, preferably one to five amino acids, and further preferably one to two amino acids are substituted in, deleted from, and/or added to the parent amino acid sequence of the variant.

In the present invention, among the above, the component (A) is preferably proinsulin, insulin, insulin B chain, a fragment thereof or a variant thereof, and further preferably human proinsulin, human insulin, human insulin B chain, a fragment thereof or a variant thereof, from the viewpoint of further enhancing the effect of prevention or treatment of type I diabetes.

In the present invention, as the component (A), one member from among proinsulin, insulin, insulin A chain, insulin B chain, a fragment thereof and a variant thereof may be used alone, or two or more members may be used in combination.

Component (B)

α-GalCer, which is used as the component (B) in the present invention, is a glycosphingolipid in which galactose and a ceramide are bonded in the α-configuration, and specific examples include, for example, those disclosed in WO 94/09020, WO 94/02168, WO 94/24142, WO 98/44928, and Science, 278, p. 1626-1629, 1997. The present invention suitably uses, as α-GalCer, KRN7000, that is, (2S,3S,4R)-1-O-(α-D-galactopyranosyl)-2-hexacosanoylamino-1,3,4-octadecanetriol, from the viewpoint of further enhancing the effect of prevention or treatment of type I diabetes.

In the present invention, α-GalCer may be formulated as a liposome. In α-GalCer that has been formulated as a liposome, i.e., an α-GalCer-containing liposome, the α-GalCer is usually localized and present in the lipid bilayer membrane of the liposome. It is possible in the present invention that the effect of prevention or treatment of type I diabetes is further effectively exerted by using an α-GalCer-containing liposome.

When α-GalCer formulated as a liposome is used, the formulation ratio of α-GalCer to be contained in the liposome is not limited in particular. For example, the amount of α-GalCer is, for example, 0.1 to 40 parts by weight, preferably 0.5 to 20 parts by weight, relative to 100 parts by weight of the total amount of the liposome forming ipids.

Lipids which are used for formulating α-GalCer as a liposome are not limited in particular, as long as they are capable of forming a bilayer membrane structure. Specifically, liposome forming lipids include diacylphosphatidylcholines, such as dipalmitoylphosphatidylcholine (DPPC), dioleoylphosphatidylcholine (DOPC), dimyristoylphosphatidylcholine (DMPC), and disteroylphosphatidylcholine (DSPC); diacylphosphatidylglycerols, such as dipalmitoylphosphatidylglycerol (DPPG), dioleoylphosphatidylglycerol (DOPG), dimyristoylphosphatidylglycerol (DMPG), and disteroylphosphatidylglycerol (DSPG); sterols, such as cholesterol, 3β-[N-(dimethylaminoethane)carbamoyl]cholesterol (DC-Chol), N-(trimethylammonioethyl)carbamoyl cholesterol (TC-Chol), tocopherol, cholesterol succinate, lanosterol, dihydrolanosterol, desmosterol, dihydrocholesterol, zymosterol, ergosterol, stigmasterol, sitosterol, campesterol, and brassicasterol; phosphatidylethanolamines, such as dioleoylphosphatidylethanolamine (DOPE), disteroylphosphatidylethanolamine (DSPE), and polyethylene glycol phosphatidylethanolamine (PEG-PE); phosphatidines, such as dimyristoylphosphatidic acid; gangliosides, such as ganglioside GM1; polyethylene glycol fatty acid esters, such as polyethylene glycol palmitate and polyethylene glycol myristilate; and others.

In the present invention, one of the liposome forming lipids may used alone, but it is preferable to use combinations of two or more of the liposome forming lipids. Preferable examples of such combinations of liposome forming lipids include a combination of a diacylphosphatidylcholine, a diacylphosphatidylglycerol and a sterol, as well as a combination of a diacylphosphatidylcholine and a sterol; further preferable examples include a combination of DOPC, DOPG, and cholesterol, a combination of DPPC, DOPC, DPPG, DOPG, and cholesterol, a combination of DPPC, DOPC, DPPG, and cholesterol, as well as a combination of DOPC and cholesterol and/or DC-Chol.

When a combination of two or more liposome forming lipids is used, the formulation ratios of the respective lipids are determined as appropriate, taking the size, fluidity, and others required for the liposome into consideration. For example, in cases where a combination of a diacylphosphatidylcholine, a diacylphosphatidylglycerol and a sterol is employed, the molar ratio among the diacylphosphatidylcholine, the diacylphosphatidylglycerol and the sterol is usually 1:0.05 to 3.0:0.05 to 6.0, preferably 1:0.1 to 1.5:0.1 to 3.0. More specifically, in cases where a combination of DOPC, DOPG and cholesterol is employed, the molar ratio among DOPC:DOPG:cholesterol is 1:0.05 to 1.0:0.05 to 3.0, preferably 1:0.1 to 0.7:0.1 to 1.5. Also, for example, in cases where a combination of DPPC, DOPC, DPPG, DOPG, and cholesterol is employed, the molar ratio among DPPC:DOPC:DPPG:DOPG:cholesterol is 1:0.25 to 2.0:0.25 to 2.0:0.25 to 2.0:1.0 to 5.0, preferably 1:0.5 to 1.5:0.5 to 1.5:0.5 to 1.5:1.5 to 3.0. Also, for example, in cases where a combination of DPPC, DOPC, DPPG, and cholesterol is employed, the molar ratio among DPPC:DOPC:DPPG:cholesterol is 1:0.16 to 1.65:0.16 to 1.0:0.16 to 1.3, preferably 1:0.4 to 0.75:0.2 to 0.5:0.3 to 0.75. For example, in cases where a combination of a diacylphosphatidylcholine (preferably DOPC) and a sterol (preferably cholesterol and/or DC-Chol) is employed, the molar ratio between the diacylphosphatidylcholine and the sterol is 1:0.05 to 4, preferably 1:0.1 to 1.

In addition, liposome constituents which are used for formulating α-GalCer as a liposome may optionally contain a cationic compound such as stearylamine and oleylamine; an anionic compound such as dicetyl phosphate; and a membrane protein, of which the formulation ratio can be determined as appropriate.

The size of α-GalCer-containing liposomes is not limited in particular, and normally the average particle diameter of the liposomes is 50 to 1000 nm, preferably 100 to 400 nm. The average particle diameter of the liposomes is measured by a dynamic light-scattering method.

The structure of α-GalCer-containing liposomes is not limited in particular, and may be of any type of MLV (multilamellar vesicle), DRV (dehydration-rehydration vesicle), LUV (large unilamellar vesicle), or SUV (small unilamellar vesicle).

A solution which is incorporated in the α-GalCer-containing liposome is a pharmaceutically acceptable aqueous carrier, such as water, a buffer solution, and physiological saline.

α-GalCer-containing liposomes are prepared by publicly known methods for preparing liposomes, such as hydration, sonication, ethanol injection, ether injection, reverse-phase evaporation, surfactant method, and freezing/thawing. Additionally, the particle size distribution of liposomes can be adjusted by passing them through a filter having a given pore size. Further, it is also possible to convert MLV liposomes to unilamellar liposomes and vice versa according to a publicly known method.

Ratio Between Components (A) and (B)

In a preparation of the present invention, the ratio between the components (A) and (B) is not limited in particular. For example, the total amount of the component (B) (in terms of the weight of α-GalCer) is 0.1 to 10,000 parts by weight, preferably 1 to 1,000 parts by weight, and further preferably 10 to 500 parts by weight, relative to the total amount of 100 parts by weight of the component (A).

Aspects of Preparations

A preparation of the present invention may be a single preparation having both the components (A) and (B) contained therein, or may be designed so that the components (A) and (B) are separately subjected to production of their respective preparations, and the preparations are mixed and administered when used or are administered separately in sequence. It is suitable, from the viewpoint of ease of use, that a preparation of the present invention is a single preparation having both the components (A) and (B) contained therein.

In a preparation of the present invention, when a single preparation having both the components (A) and (B) contained therein is prepared using, as the component (B), α-GalCer that has been formulated as a liposome, the component (A) may be subjected to production of the single preparation in a state where it is not encapsulated in the liposome containing the component (B). However, it is desirable that from the viewpoint of further effectively exerting the effect of prevention or treatment of type I diabetes, the component (A) is subjected to production of the single preparation in a state where it is encapsulated (incorporated) in the liposome containing the component (B) (the lipid bilayer membrane or the aqueous phase within the liposome). Encapsulation of the component (A) in the liposome containing the component (B) can be carried out by publicly known methods, such as hydration, sonication, ethanol injection, ether injection, reverse-phase evaporation, surfactant method, and freezing/thawing.

The dosage form of a preparation of the present invention may be a liquid form or a dry form. When a preparation of the present invention is in a liquid form, the components (A) and (B) should be dissolved or suspended, for example, in a buffer solution, such as physiological saline, a phosphate buffer, a citrate buffer, and an acetate buffer. When a preparation of the present invention is in a dry form, the preparation is used after a buffer solution, such as physiological saline, a phosphate buffer, a citrate buffer, and an acetate buffer is added so that the preparation may have a liquid form.

A preparation of the present invention may optionally contain a pharmaceutically acceptable additive or additives, such as a sugar, a polyhydric alcohol, a water-soluble polymer, a non-ionic surfactant, an anti-oxidant, and a pH adjusting agent.

Administration Methods

A preparation of the present invention is administered via subcutaneous, intramuscular, intravenous, intraperitoneal, intraarticular, or mucosal administration, or the like. Among these modes of administration, subcutaneous administration, intramuscular administration, and intraperitoneal administration are preferable, with subcutaneous or intraperitoneal administration being most preferable. Especially, subcutaneous or intraperitoneal administration of a preparation of the present invention makes the effect of prevention or treatment of type I diabetes even more remarkable.

A subject for the administration of a preparation of the present invention is a human who is in need of the prevention or treatment of type I diabetes, and preferably includes, for example, humans who are at risk of developing type I diabetes (have genetic predisposition or the like to develop type I diabetes) and humans who have developed type I diabetes. A preparation of the present invention can be said to be a breakthrough medicament in that since it is capable of direct suppression of the induction of CTLs specifically attacking pancreatic β cells, type I diabetes can be prevented or treated straightforwardly, in contrast to traditional symptomatic treatments including insulin administration. Therefore, even if the subject intended for administration is a patient who traditionally needs insulin administration during his/her life, by applying a preparation of the present invention to the patient, it is possible to significantly increase the possibility that the patient will be freed from such insulin administration.

As mentioned above, a preparation of the present invention uses a mechanism different from the previously reported mechanism in which the production of allergen-specific antibodies and autoantibodies is inhibited using α-GalCer. Particularly, a remarkable preventive effect against type I diabetes is obtained through the suppression of the induction of CTLs specifically attacking pancreatic β cells. Therefore, a preparation of the present invention is suitably used for humans who are in need of the prevention of type I diabetes, especially, humans who are at risk of developing type I diabetes.

Furthermore, a preparation of the present invention is capable of inducing the expression of suppressive cytokines. Suppressive cytokines include, for example, IL-2 and IL-10. In addition, a preparation of the present invention is capable of inducing cells such as plasmacytoid dendritic cells (pDCs) and allowing these cells to gather in the pancreatic lymph nodes so that a subset of suppressive T cells involved in the treatment is induced and allowed to gather in a pancreas-specific manner, thereby making it possible to induce antigen-specific regulatory T cells.

It is assumed that immunosuppressive cytokines induced by a preparation of the present invention result from secretion from antigen-specific regulatory T cells induced by the preparation.

From the above, a preparation of the present invention, when used in a state where insulin has been incorporated in a liposome containing α-GalCer, has an effect of inducing cells such as plasmacytoid dendritic cells (pDCs) and allowing these cells to gather in the pancreatic lymph nodes so that a subset of suppressive T cells involved in the treatment is induced and allowed to gather in a pancreas-specific manner and pathogenic Th1 cells are effectively removed. In addition, the destruction of the pancreas can be blocked by direct suppression of the induction of and removal of CTLs specifically attacking pancreatic β cells.

Dosage amounts of a preparation of the present invention should be amounts effective for the prevention or treatment of type I diabetes, and are determined as appropriate, depending on the age, weight, and degree of the symptom of the subject intended for administration. For example, the dosage amount may be determined such that the component (A) is administered once to several times a day, preferably once a day, in an amount of approximately 0.5 to 5000 µg/kg of body weight. Further, a preparation of the present invention may be administered for a period of one day or several successive days, or at intervals of one day or several days.

EXAMPLES

The present invention will now be described in more detail with reference to examples, which are not intended to limit the present invention. The examples which follow used KRN7000 as α-GalCer.

Example 1

Production of an Insulin-B-Peptide-Incorporated α-GalCer-Liposome

L-α-Phosphatidylcholine, Dioleoyl (DOPC; Wako Pure Chemical Industries, Ltd.), 1,2-Dioleoyl-sn-Glycero-3-[Phospho-rac-(1-glycerol)] (Sodium Salt) (DOPG; Wako Pure Chemical Industries, Ltd.), and Cholesterol (plant derived) (Avanti) were mixed at a molar ratio of 5:2:3, and then 10 mg of the mixture was dissolved in 1000 µl of a solvent of chloroform/methanol (1:1 by volume). Separately, 0.2 mg of α-GalCer was dissolved in 100 µl of the chloroform/methanol solvent. These solutions were mixed, followed by removal of the organic solvents using an evaporator to form a thin film of the lipids containing α-GalCer on the bottom surface of the eggplant flask. Further, the organic solvents were completely removed from the lipid film by drying overnight in a vacuum desiccator. To the lipid film was added a 50 mM Tris-HCl buffer (pH 8.5) containing 1 mg/ml of a fragment of human insulin B chain (B:9-23) (sometimes referred to hereinafter as an insulin B peptide), and the lipid film was completely hydrated by vortexing. The resulting product was subjected to freezing/thawing treatment 4 times or more, followed by passing it through a 200-nm polycarbonate membrane (Avanti) several times. Finally, unincorporated peptide was completely removed by dialysis to prepare a solution containing an insulin-B-peptide-incorporated α-GalCer-containing liposome (referred to hereinafter as an insulin-B-peptide GalCer-liposome solution). The insulin-B-peptide GalCer-liposome solution had a final concentration of α-GalCer of 200 μg/ml and a final concentration of insulin B peptide (B:9-23) of 500 μg/ml.

Example 2

Assessment of Drug Efficacy of an Insulin-B-Peptide-Incorporated α-GalCer-Liposome in the Prevention of the Onset of Type I Diabetes 1. Materials and Methods
1-1. Production of an Insulin-B-Peptide-Incorporated α-GalCer-Liposome and Preparation of a Sample for Administration The insulin-B-peptide-incorporated α-GalCer-containing liposome produced in Example 1 was used. 10 μl of the insulin-B-peptide GalCer-liposome solution prepared in Example 1 (corresponding to 2 μg of α-GalCer and 5 μl of insulin B-peptide) and 90 μl of physiological saline were mixed to prepare a sample for administration.

1-2. Production of an Insulin-B-Peptide-Incorporated Liposome and Preparation of a Sample for Administration L-α-Phosphatidylcholine, Dioleoyl (DOPC: Wako Pure Chemical Industries, Ltd.), 1,2-Dioleoyl-sn-Glycero-3-[Phospho-rac-(1-glycerol)] (Sodium Salt) (DOPG: Wako Pure Chemical Industries, Ltd.), and Cholesterol (plant derived) (Avanti) were mixed at a molar ratio of 5:2:3, and then 10 mg of the mixture was dissolved in 1000 μl of a solvent of chloroform/methanol (1:1 by volume). After that, the organic solvents were removed using an evaporator to form a lipid thin film on the bottom surface of the eggplant flask. Further, the organic solvents were completely removed from the lipid film by drying overnight in a vacuum desiccator. To the lipid film was added 1 ml of a 50 mM Tris-HCl buffer (pH 8.5) containing 3 mg/ml of a fragment of the insulin B chain (B:9-23) (sometimes referred to hereinafter as an insulin B peptide), and the lipid film was completely hydrated by vortexing. The resulting product was subjected to freezing/thawing treatment 4 times or more, followed by passing it through a 200-nm polycarbonate membrane (Avanti) several times. Finally, unincorporated peptide was completely removed by dialysis to prepare a solution containing an insulin-B-peptide-incorporated liposome (referred to hereinafter as an insulin-B-peptide liposome solution). The resulting liposome solution had a final concentration of insulin B-peptide (B:9-23) of 500 μg/ml.

10 μl of the liposome solution thus obtained (corresponding to 5 μg of peptide) and 90 μl of physiological saline were mixed to prepare a sample for administration.

1-3. Production of an OVA-Peptide-Incorporated α-GalCer-Liposome and Preparation of a Sample for Administration L-α-Phosphatidylcholine, Dioleoyl (DOPC; Wako Pure Chemical Industries, Ltd.), 1,2-Dioleoyl-sn-Glycero-3-[Phospho-rac-(1-glycerol)] (Sodium Salt) (DOPG; Wako Pure Chemical Industries, Ltd.), and Cholesterol (plant derived) (Avanti) were mixed at a molar ratio of 5:2:3, and then 10 mg of the mixture was dissolved in 1000 μl of a solvent of chloroform/methanol (1:1 by volume). Separately, 0.2 mg of α-GalCer was dissolved in 100 μl of the chloroform/methanol solvent. These solutions were mixed, followed by removal of the organic solvents using an evaporator to form a thin film of the lipids containing α-GalCer on the bottom surface of the eggplant flask. Further, the organic solvents were completely removed from the lipid film by drying overnight in a vacuum desiccator. To the lipid film was added sterile distilled water containing 1 mg/ml of an OVA peptide (an ovalbumin peptide, 323-339), and the lipid film was completely hydrated by vortexing. The resulting product was subjected to freezing/thawing treatment 4 times or more, followed by passing it through a 200-nm polycarbonate membrane (Avanti) several times. Finally, unincorporated peptide was completely removed by dialysis to prepare a solution containing an OVA-peptide-incorporated α-GalCer-liposome (referred to hereinafter as an OVA-peptide GalCer-liposome solution). The resulting liposome solution had a final concentration of α-GalCer of 200 μg/ml and a final concentration of OVA peptide of 500 μg/ml.

10 μl of the liposome solution thus obtained (corresponding to 2 μg of α-GalCer and 5 μg of OVA peptide) and 90 μl of physiological saline were mixed to prepare a sample for administration.

1-4. Assessment of Drug Efficacy Using NOD Mice (Dosing Conditions and Measurement of Blood Glucose Concentrations)

To NOD mice (NOD/ShiLtJ, The Jackson Laboratory, CA, USA), which are animal models for type I diabetes, was administered intraperitoneally 100 μl of the sample for administration, twice a week between the age of 4 to 8 weeks, which was a period prior to the onset of type I diabetes. The concentration of glucose in the blood was measured every second week. NOD mice were divided into five test groups: 1) a group receiving no drug (i.e., a group receiving physiological saline), 2) a group receiving the insulin-B-peptide-incorporated α-GalCer-liposome, 3) a group receiving the insulin-B-peptide-incorporated liposome, and 4) a group receiving the OVA-peptide-incorporated α-GalCer-liposome, with 10 mice per group. For measuring the concentration of glucose, a commercially available apparatus for measuring blood glucose levels (ACCU-CHEK Aviva, Roche) was used, which is intended for diabetes patients. The determination of the onset of diabetes was based on the criterion according to which a mouse was considered to have developed diabetes when the mouse had a blood glucose concentration of 250 mg/dL or higher. The incidence of diabetes was expressed as percentage (%) of individuals having developed diabetes in a group of the mice receiving the same sample. Schematic structures of the respective samples for administration used in the test are depicted in FIG. 1.

2. Results and Discussion

Figure 2:
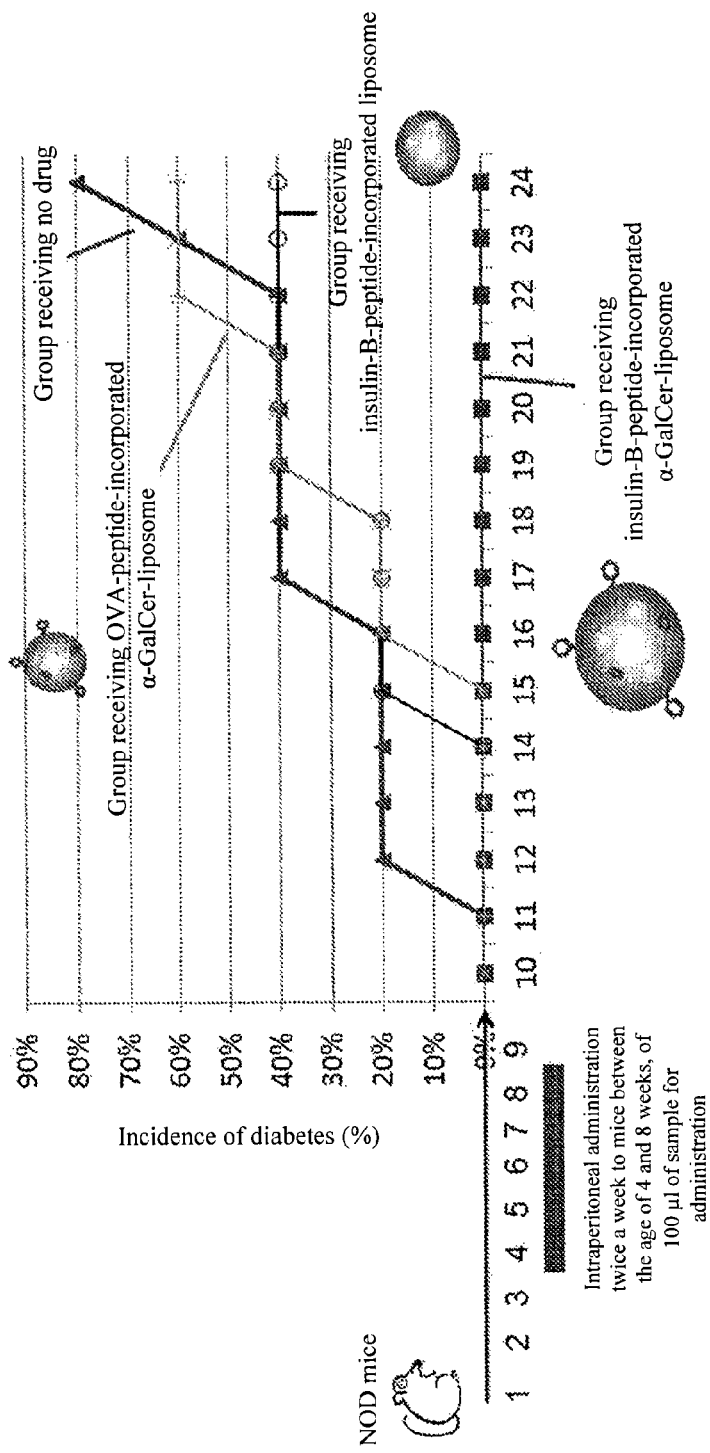
FIG. 2 shows the results obtained by evaluating the incidence of diabetes over time in each of the test groups in Example 2.

The results obtained by evaluating the incidence of type I diabetes over time are shown in FIG. 2. As can be seen from FIG. 2, the group receiving no drug (triangles) began to display symptoms at weeks 11 to 12, with about a half of the mice developing diabetes at weeks 16 to 17 and about 80% at week 24. In contrast, the group receiving the insulin-B-peptide-incorporated α-GalCer-liposome (squares) did not exhibit an increase in blood sugar levels and provided 100% of preventive effect against the onset of the disease at the time when 24 weeks passed. The group receiving the insulin-B-peptide-incorporated liposome (open circles), on the other hand, had a greater contribution to delaying the onset of the disease than the group receiving no drug, but about 40% of the mice developed diabetes at week 24. The group receiving the OVA-peptide-incorporated α-GalCer-liposome (asterisks), in which the OVA peptide, a non-insulin peptide, had been incorporated, also had a greater contribution to delaying the onset of the disease than the group receiving no drug, while later on, having faster progress of the disease than the group receiving no drug, with about 60% of the mice developing diabetes at week 24. From these results, it has been ascertained that the combination of the insulin peptide and α-GalCer is important for preventing the onset of type I diabetes and that the insulin-B-peptide-incorporated α-GalCer-liposome can be an efficacious and effective medicament for preventing the onset of type I diabetes.

Example 3

Test for Assessment of the Induction of Insulin-B-Peptide-Specific Treg Cells Using Spleen Cells Derived from Drug-Administered NOD Mice 1. Materials and Methods
1-1. Production of an Insulin-B-Peptide-Incorporated α-GalCer-Liposome and Preparation of a Sample for Administration The insulin-B-peptide-incorporated α-GalCer-containing liposome produced in Example 2 was used. 10 µl of the liposome solution of the insulin-B-peptide-incorporated α-GalCer-containing liposome (corresponding to 2 µg of α-GalCer and 5 µg of insulin B peptide) and 90 ml of physiological saline were mixed to prepare a sample for administration.

1-2. Production of an Insulin-B-Peptide-Incorporated Liposome and Preparation of a Sample for Administration The insulin-B-peptide-incorporated liposome produced in Example 2 was used. 10 µl of the liposome solution of the insulin-B-peptide-incorporated liposome (corresponding to 5 µg of insulin B peptide) and 90 µl of physiological saline were mixed to prepare a sample for administration.

1-3. Production of an α-GalCer-Liposome and Preparation of a Sample for Administration L-α-Phosphatidylcholine, Dioleoyl (DOPC; Wako Pure Chemical Industries, Ltd.), 1,2-Dioleoyl-sn-Glycero-3-[Phospho-rac-(1-glycerol)] (Sodium Salt) (DOPG; Wako Pure Chemical Industries, Ltd.), and Cholesterol (plant derived) (Avanti) were mixed at a molar ratio of 5:2:3, and then 10 mg of the mixture was dissolved in 1000 µl of a solvent of chloroform/methanol (1:1 by volume). Separately, 0.2 mg of α-GalCer was dissolved in 100 µl of the chloroform/methanol solvent. These solutions were mixed, followed by removal of the organic solvents using an evaporator to form a thin film of the lipids containing α-GalCer on the bottom surface of the eggplant flask. Further, the organic solvents were completely removed from the lipid film by drying overnight in a vacuum desiccator. To the lipid film was added distilled water, and the lipid film was completely hydrated by vortexing and sonication. Finally, the resulting product was passed through a 200-nm polycarbonate membrane (Avanti) several times to prepare a solution of an α-GalCer-containing liposome (hereinafter referred to as a GalCer-liposome solution). The resulting liposome solution had a final concentration of α-GalCer of 200 µg/ml.

10 µl of the liposome solution thus obtained (corresponding to 2 µg of α-GalCer) and 90 µl of physiological saline were mixed to prepare a sample for administration.

1-4. Production of an α-GalCer Solution and Preparation of a Sample for Administration To 3 mg of α-GalCer (KRN7000 powder) was added 3 ml of dimethyl sulfoxide (DMSO), and the α-GalCer was dissolved in a high-temperature layer at 80° C. To the solution was added 12 ml of PBS(−) containing 0.5% Tween 80, and the mixture was mixed. This resulted in to a solution having a final concentration of α-GalCer of 200 µg/ml, which was used as a stock solution. 10 µl of the stock solution thus obtained (corresponding to 2 µg of α-GalCer) and 90 µl of physiological saline were mixed to prepare a sample for administration.

1-5. Analysis of Insulin-B-Peptide-Specific Cell Proliferation of Treg Cells and Measurement of Cytokine Production To NOD mice (NOD/ShiJcl, CLEA Japan Inc., Tokyo, Japan), which are animals representing a spontaneous model for type I diabetes, was intraperitoneally administered 100 µl of the sample for administration, twice a week between the age of 5 to 10 weeks, which was a period prior to the onset of type I diabetes. The spleen was removed from 13-week-old mice and then spleen cells were prepared and subjected to cell culture. Groups receiving test drugs were the following five groups: 1) a group receiving no drug (i.e., a group receiving physiological saline), 2) a group receiving the insulin-B-peptide-incorporated α-GalCer-liposome, 3) a group receiving the insulin-B-peptide-incorporated liposome, 4) a group receiving the α-GalCer-liposome, and 5) a group receiving the α-GalCer solution, with N=2 to 3 animals per group. After preparation of spleen cells from the animals of each of the groups, spleen cells were loaded with CFSE (carboxyfluorescein diacetate succinimidyl ester), a dye used in cell proliferation assays, and subjected to reaction, followed by washing the cells to remove the dye, in regular procedures. Finally, in order to examine the antigen specificity of cells, CFSE-labeled cells from each group were loaded with a) no added antigen, b) insulin B peptide, or c) a non-insulin peptide (OVA peptide), and cultured in a $CO_2$ incubator for four days. After culturing, cultured cells and culture supernatant were collected. The cells were subjected to FACS analysis of the increase in CFSE in the population of CD4(+) Foxp3(+) cells, and the supernatant was used for measuring the amounts of produced cytokines in the supernatant. The concentrations of IL-2 and IL-10 in the culture supernatant were also measured.

2. Results and Discussion

Figure 3:
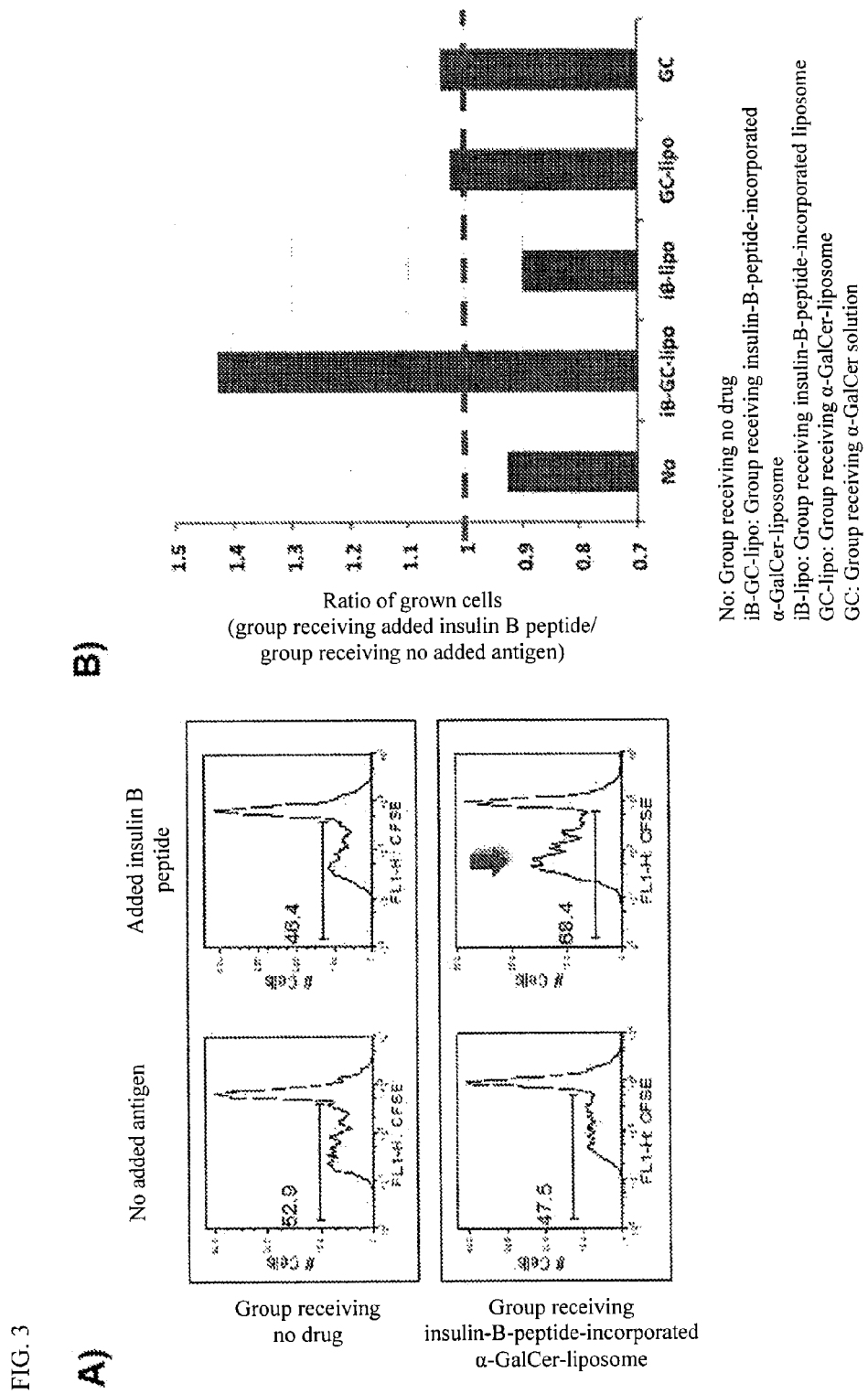
FIG. 3 shows the results obtained by measuring the growth of insulin B peptide-specific Treg cells in each of the test groups (FIG. 3A) and by determining the ratios of cells grown in the absence of added antigen and in the presence of added insulin B peptide in Example 3 (FIG. 3B).

Spleen cells were prepared from NOD mice of different groups receiving different drugs and analyzed for the proliferation of antigen-specific Treg cells by culturing them in the presence of added insulin B peptide. In the group receiving no drug, the percentage of CFSE proliferated cells in the population of CD4(+) Foxp3(+) cells after the culture was about 55% when no antigen was added, and about 51% when the insulin B peptide was added, and thus the proliferation of Treg cells specific for the insulin B peptide was not observed (FIG. 3A, upper panel). In contrast, in the group receiving the insulin-B-peptide-incorporated α-GalCer-liposome, the percentage of CFSE proliferated cells in the population of CD4(+) Foxp3(+) cells after the culture was about 45% when no antigen was added, and about 64% when the insulin B peptide was added, and thus antigen-specific proliferation of Treg cells by the addition of the insulin B peptide was observed (FIG. 3A, lower panel). The ratio of the percentage of proliferated cells when no antigen was added to the percentage when the insulin B peptide was added (FIG. 3B) was 0.93 for the group receiving no drug, and in contrast, 1.43 for the group receiving the insulin-B-peptide-incorporated α-GalCer-liposome, revealing that the proliferation of Treg cells was caused to increase by 1.5 times or more relative to the group receiving no drug. The group receiving the insulin-B-peptide-containing liposome had a ratio of 0.90, the group receiving α-GalCer-liposome had a ratio of 1.02, and the group receiving the α-GalCer solution had a ratio of 1.04, relative to the group receiving no drug, and thus the proliferation of antigen-specific Treg cells was not observed in any of these groups.

When the amounts of cytokines produced into the culture supernatant were measured, it was shown that the production of IL-2 and IL-10, cytokines associated with immunosuppression that are assumed to result from Treg cells, was significantly induced only in the group receiving the insulin-B-peptide-incorporated α-GalCer-liposome (Table 1). In similar experiments using the non-insulin peptide, there were not observed the induction of Treg cells and the induction of the production of suppressive cytokines in any of the test groups.

TABLE 1

|  | Concentration of IL-2 in culture supernatant (pg/ml) | Concentration of IL-10 in culture supernatant (pg/ml) |
| --- | --- | --- |
| Group receiving no drug | 1.1 | 0.7 |
| Group receiving insulin-B-peptide-incorporated α-GalCer-liposome | 14.8 | 9.8 |
| Group receiving insulin-B-peptide-incorporated liposome | 3.4 | 1.9 |
| Group receiving α-GalCer-liposome | 0.8 | 0.9 |
| Group receiving α-GalCer solution | 0.9 | 1.3 |

From the above, it was shown that the administration of the insulin-B-peptide-incorporated α-GalCer-liposome causes the induction of insulin-B-peptide-specific Treg cells which would be involved in the prevention of the onset of type I diabetes, and the induction of these cells requires the combination of the insulin B peptide and α-GalCer. It is assumed that the induction of these antigen-specific Treg cells will contribute to the preventive effect against the onset of diabetes which was observed in the NOD mice experiments.

Example 4

Assessment of Drug Efficacy of Insulin-Incorporated α-GalCer-Liposome in the Prevention of the Onset of Type I Diabetes and Search for Routes of Administration 1. Materials and Methods
1-1. Production of an Insulin-Incorporated α-GalCer-Liposome and Preparation of a Sample for Administration L-α-Phosphatidylcholine, Dioleoyl (DOPC; Avanti Polar Lipids, Inc.), 1,2-Dipalmitoyl-sn-glycero-3-phosphocholine (DPPC; Avanti), 1,2-Dioleoyl-sn-glycero-3-phosphoglycerol, sodium salt (DOPG; Avanti), 1,2-Dipalmitoyl-sn-glycero-3-phosphoglycerol, sodium salt (DPPG; Avanti), and Cholesterol (plant derived) (Avanti) were mixed at a molar ratio of 1.5:1.5:1.5:1.5:4, and then 50 mg of the mixture was dissolved in a solvent of chloroform/methanol (1:1 by volume). Under a stream of nitrogen gas, the organic solvents were removed using an evaporator, and further the remaining organic solvents were completely removed by a freeze-drying method. The dried lipid mixture was dissolved in 90% tert-butanol at 50° C., and α-GalCer was added so that the volume was 5% by weight and dissolved. The solution was frozen, and then dried by freeze-drying. Subsequently, 2.5 ml of a solution of insulin (recombinant human insulin, manufactured by Invitrogen; in 10 mM HCl/2% glycine) was added to the dried lipid mixture, which was then subjected to complete hydration, followed by three rounds of freezing/thawing treatment. The resulting solution was passed through an 800-nm polycarbonate membrane (Avanti) 5 times, and then through a 200-nm polycarbonate membrane (Avanti) 5 times to make the particle diameter uniform. To this solution was added a 5 times volume of PBS, and the pH was adjusted to about 7, resulting in precipitates of unincorporated insulin. Centrifugation was performed at 10,000 rpm for 15 minutes to separate and remove the unincorporated insulin. Finally, the supernatant was diluted 10 times with PBS to prepare a solution containing an insulin-incorporated α-GalCer-containing liposome (referred to hereinafter as an insulin GalCer-liposome solution). The resulting liposome solution had a final concentration of α-GalCer of 20 μg/ml and a final concentration of insulin of 200 μg/ml.

1-2. Assessment of Drug Efficacy Using NOD Mice (Dosing Conditions and Measurement of Blood Glucose Concentrations)

To NOD mice (NOD/ShiLtJ, The Jackson Laboratory, CA, USA) was administered via subcutaneous, tail vein or intraperitoneal administration 50 μl of the insulin-incorporated α-GalCer-liposome solution prepared in the section 1-1, twice a week between the age of 4 to 8 weeks, which was a period prior to the onset of type I diabetes. The concentration of glucose in the blood was measured every second week. For measuring the concentration of glucose in the blood, a commercially available apparatus for measuring blood glucose levels (ACCU-CHEK Aviva, Roche) was used, which is intended for diabetes patients. The determination of the onset of diabetes was based on the criterion according to which a mouse was considered to have developed diabetes when the mouse had a blood glucose concentration of 250 mg/dL or higher. The incidence of diabetes was expressed as percentage (%) of individuals having developed diabetes in a group of the mice receiving the same sample.

2. Results and Discussion

Figure 4:
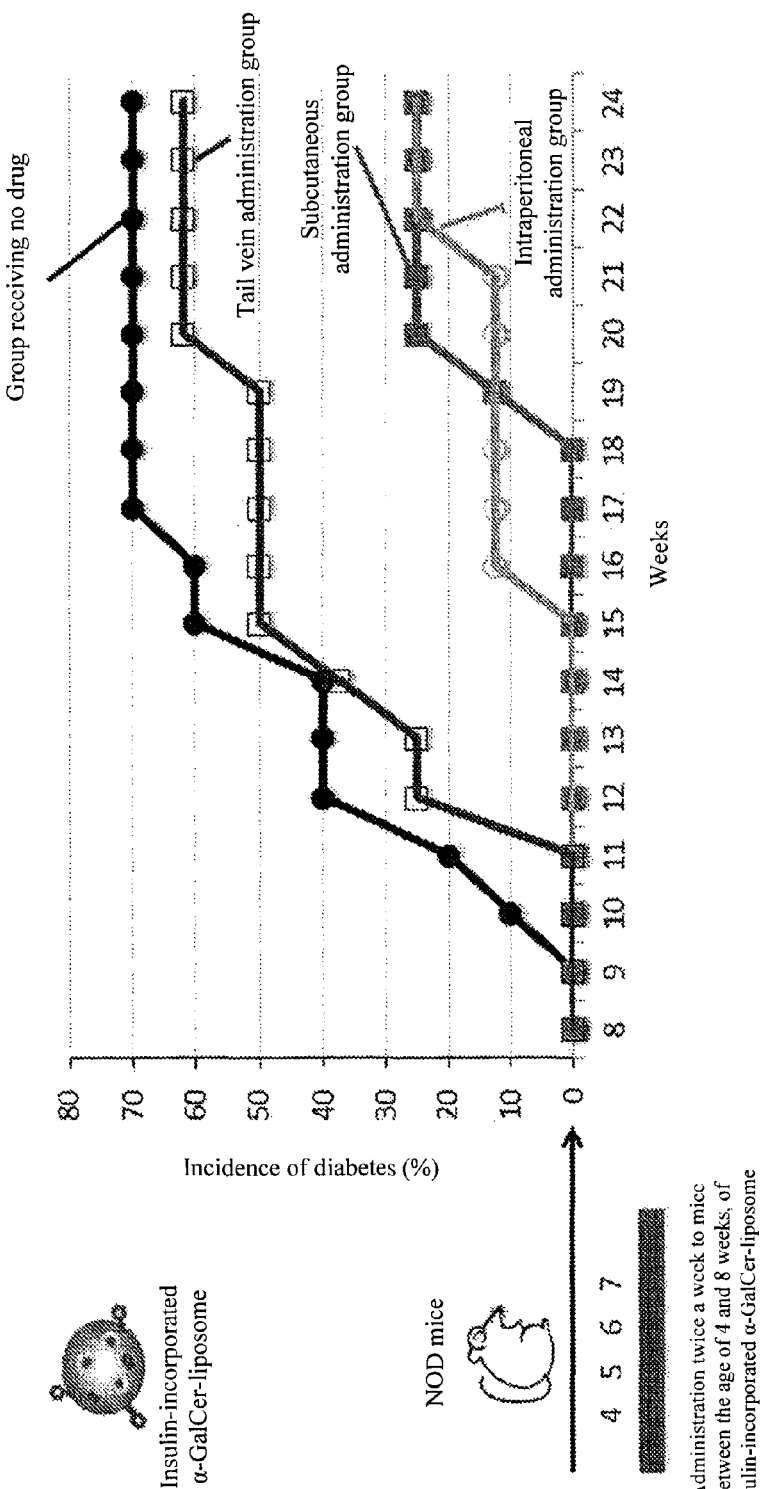
FIG. 4 shows the results obtained by evaluating the incidence of type I diabetes over time in each of the test groups, where the route of administration was changed, in Example 4.

The results obtained by evaluating the incidence of type I diabetes over time are shown in FIG. 4. The group receiving no drug (closed circles) began to display symptoms at weeks 9 to 10, with about a half of the mice developing diabetes at weeks 14 to 15 and about 70% at week 24. In contrast, it was shown that in the group receiving subcutaneous administration of the insulin-incorporated α-GalCer-liposome (squares), the onset of diabetes occurred at weeks 18 to 19 (i.e., the onset of diabetes was delayed), and the percentage of mice having developed diabetes at week 24 was 25% and thus the incidence of diabetes was significantly decreased. A similar effect was observed in the intraperitoneal administration group (open circles), in which the onset of diabetes occurred at weeks 11 to 12 and the incidence of diabetes was decreased to 25% at the time of week 24. The tail vein administration group (open squares), on the other hand, showed slightly delayed onset of diabetes and a decreased incidence of diabetes (the incidence of diabetes at week 24 was 62%), and at the same time, was found to have weaker effects, compared to the subcutaneous and intraperitoneal administration groups.

Example 5

Effects of Suppressing the Proliferation of Cytotoxic T Cells (CTLs) Specific for Pancreatic β Cells by Administration of Insulin-Incorporated α-GalCer-Liposome 1. Materials and Methods 1-1. Production of an Insulin-Incorporated α-GalCer-Liposome and Preparation of a Sample for Administration The insulin-incorporated α-GalCer-containing liposome produced in Example 4 was used as a sample for administration.

1-2. Production of an Insulin-Incorporated Liposome and Preparation of a Sample for Administration L-α-Phosphatidylcholine, Dioleoyl (DOPC; Avanti Polar Lipids, Inc.), 1,2-Dipalmitoyl-sn-glycero-3-phosphocholine (DPPC; Avanti), 1,2-Dioleoyl-sn-glycero-3-phosphoglycerol, sodium salt (DOPG; Avanti), 1,2-Dipalmitoyl-sn-glycero-3-phosphoglycerol, sodium salt (DPPG; Avanti), and Cholesterol (plant derived) (Avanti) were mixed at a molar ratio of 1.5:1.5:1.5:4, and then 50 mg of the mixture was dissolved in a solvent of chloroform/methanol (1:1 by volume). Under a stream of nitrogen gas, the organic solvents were removed using an evaporator, and further the remaining organic solvents were completely removed by a freeze-drying method. 2.5 ml of a solution of insulin (recombinant human insulin, manufactured by Invitrogen; in 10 mM HCl/2% glycine) was added to the dried lipid mixture, which was then subjected to complete hydration, followed by three rounds of freezing/thawing treatment. The resulting solution was passed through an 800-nm polycarbonate membrane (Avanti) 5 times, and then through a 200-nm polycarbonate membrane (Avanti) 5 times to make the particle diameter uniform. To this solution was added a 5 times volume of PBS, and the pH was adjusted to about 7, resulting in precipitates of unincorporated insulin. Centrifugation was performed at 10,000 rpm for 15 minutes to separate and remove the unincorporated insulin. Finally, the supernatant was diluted 10 times with PBS to prepare a solution containing an insulin-incorporated liposome (referred to hereinafter as an insulin liposome solution). The resulting liposome solution had a final concentration of insulin of 200 μg/ml.

1-3. Production of an α-GalCer-Liposome and Preparation of a Sample for Administration L-α-Phosphatidylcholine, Dioleoyl (DOPC; Avanti Polar Lipids, Inc.), 1,2-Dipalmitoyl-sn-glycero-3-phosphocholine (DPPC; Avanti), 1,2-Dioleoyl-sn-glycero-3-phosphoglycerol, sodium salt (DOPG; Avanti), 1,2-Dipalmitoyl-sn-glycero-3-phosphoglycerol, sodium salt (DPPG; Avanti), and Cholesterol (plant derived) (Avanti) were mixed at a molar ratio of 1.5:1.5:1.5:4, and then 50 mg of the mixture was dissolved in a solvent of chloroform/methanol (1:1 by volume). Under a stream of nitrogen gas, the organic solvents were removed using an evaporator, and further the remaining organic solvents were completely removed by a freeze-drying method. The dried lipid mixture was dissolved in 90% tert-butanol at 50° C., and α-GalCer was added so that the volume was 5% by weight and dissolved. The solution was frozen, and then dried by freeze-drying. 2.5 ml of a solution of 10 mM HCl/2% glycine was added to the dried lipid mixture, which was then subjected to complete hydration, followed by three rounds of freezing/thawing treatment. The resulting solution was passed through an 800-nm polycarbonate membrane (Avanti) 5 times, and then through a 200-nm polycarbonate membrane (Avanti) 5 times to make the particle diameter uniform. To the resulting solution was added a 5 times volume of PBS, and the pH was adjusted to about 7. Finally, the solution was diluted 10 times with PBS to prepare a solution containing an α-GalCer-containing liposome (referred to hereinafter as a GalCer-liposome solution). The resulting liposome solution had a final concentration of α-GalCer of 20 μg/ml.

1-4. Measurement of Pancreatic β Cell-Specific CTLs in Peripheral Blood Mononuclear Cells Type I diabetes is caused by insulin-producing pancreatic islets being attacked and destroyed by the autoimmune system, and in their destruction there are involved cytotoxic T cells (CTLs) that specifically recognize and attack pancreatic β cells. Therefore, the suppression of the production of, and the inactivation of such CTLs are synonymous with preventing the destruction of the pancreatic islets, leading to preventing the onset of type I diabetes or inhibiting the progress of type I diabetes. In this test, the effect of suppressing the production of pancreatic β cell-specific CTLs by administration of different preparations was evaluated. As a measurement method, a tetramer method was employed which allows quantitative analysis of the production of pancreatic β cell-specific CTLs (see the following reference: "Prediction of spontaneous autoimmune diabetes in NOD mice by quantification of autoreactive T cells in peripheral blood," Trudeau J D, Kelly-Smith C, Verchere C B, Elliott J F, Dutz J P, Finegood D T, Santamaria P, Tan R., J Clin Invest. 2003 January; 111(2):217-23). Such CTLs present in the population of peripheral blood mononuclear cells (PBMCs) isolated from NOD mice receiving different preparations were evaluated by cellular analysis (FACS analysis).

To NOD mice was intraperitoneally administered 50 μl of a sample for administration, twice a week from the age of 4 weeks, which was prior to the onset of type I diabetes. NOD mice were divided into four test groups: 1) a group receiving no drug (i.e., a group receiving physiological saline), 2) a group receiving the insulin-incorporated α-GalCer-liposome, 3) a group receiving the insulin-incorporated liposome, and 4) a group receiving the α-GalCer-liposome, with N=8 animals per group, except that N=6 for the group receiving the insulin-incorporated liposome. PBMCs were isolated from 8-week-old NOD mice in a regular procedure and subjected to reaction with a tetramer NRP-V7, which is recognized by pancreatic β cell-specific CTLs (see the following references: "Prediction of spontaneous autoimmune diabetes in NOD mice by quantification of autoreactive T cells in peripheral blood," Trudeau J D, Kelly-Smith C, Verchere C B, Elliott J F, Dutz J P, Finegood D T, Santamaria P, Tan R., J Clin Invest. 2003 January; 111(2): 217-23), followed by quantitative analysis (FACS analysis) of pancreatic β cell-specific CTLs.

2. Results and Discussion

Figure 5:
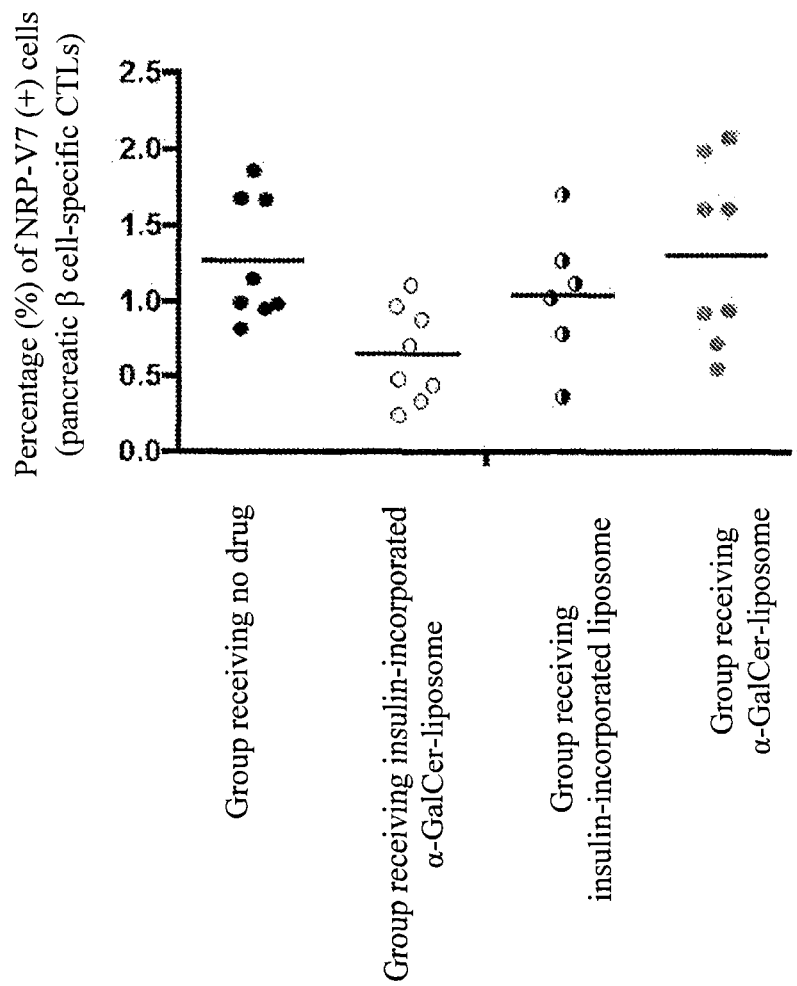
FIG. 5 shows the results obtained by determining the percentage (%) of NRP-V7 (+) cells (pancreatic β cell-specific CTLs) present in the population of B220(−) CD8(+) cells in each of the test groups in Example 5.

The results obtained by determining the percentage (%) of NRP-V7(+) cells, i.e. pancreatic β cell-specific CTLs, which are present in the subgroup of B220(−) CD8(+) cells in the population of PBMCs are shown in FIG. 5. The group receiving no drug had a percentage of these CTLs of 1.25% or higher, whereas the group receiving the insulin-incorporated α-GalCer-liposome had a percentage of these CTLs of about 0.6%, and thus exhibited a significant effect of suppressing their production. This percentage value was the same as that which was measured in the NOD mice prior to the onset of type I diabetes. It was proved from this that the administration of the insulin-incorporated α-GalCer-liposome can achieve complete suppression of the production of pancreatic β cell-specific CTLs. The group receiving the insulin-incorporated liposome and the group receiving the α-GalCer-liposome, on the other hand, had percentages of these CTLs of 1.0% and 1.25%, respectively, which were approximately the same as the percentage value of the group receiving no drug. This indicates that the administration of insulin or α-GalCer alone cannot achieve sufficient suppression of the production of such CTLs and the combination of insulin and α-GalCer is crucial for exerting the drug efficacy.

From these results, it was proved that the insulin-incorporated α-GalCer-liposome is an agent capable of preventing the onset of type I diabetes by suppressing the production of pancreatic β cell-specific CTLs and in addition, can be a breakthrough agent capable also of preventing diabetes from becoming more serious, since it is theoretically possible to induce the inactivation of such CTLs if the liposome is used at an early stage of the onset of the disease.

Example 6

Examples of Preparations (1) Preparations Containing a Human Insulin-B-Peptide-Incorporated α-GalCer-Containing Liposome The human insulin-B-peptide-incorporated α-GalCer-containing liposome obtained in Example 1 and physiological saline are mixed to prepare a preparation containing the human insulin-B-peptide-incorporated α-GalCer-containing liposome.

(2) Preparations Containing a Human Insulin-Incorporated α-GalCer-Containing Liposome A preparation containing a human insulin-incorporated α-GalCer-containing liposome is prepared by a similar method as in (1) described above, except that the human insulin-incorporated α-GalCer-containing liposome in (1) is changed to the human insulin-incorporated α-GalCer-containing liposome produced in Example 4.

(3) Preparations Containing a Human Proinsulin-Incorporated α-GalCer-Containing Liposome A human proinsulin-incorporated α-GalCer-containing liposome and physiological saline are mixed to prepare a preparation containing the human proinsulin-incorporated α-GalCer-containing liposome, wherein the human proinsulin-incorporated α-GalCer-containing liposome is produced by a similar method as in Example 4, except that in Example 4, human insulin is changed to human proinsulin.

Example 7

Examples of Use of Preparations

Any of the preparations obtained in Example 6, a preparation containing a human insulin-B-peptide-incorporated α-GalCer-containing liposome, a preparation containing a human insulin-incorporated α-GalCer-containing liposome, and a preparation containing a human proinsulin-incorporated α-GalCer-containing liposome, is usually administered to an eligible patient under conditions where the preparation is subcutaneously administered once to thrice a week for a period of 1 to 6 weeks, in an amount of 0.01 to 1.0 mg of α-GalCer per kg of body weight per dose.

The invention claimed is:

1. A preparation for prevention or treatment of type I diabetes, comprising (A) at least one member selected from the group consisting of insuiin B chain, fragments thereof and variants thereof and (B) KRN7000,
wherein the components (A) and (B) are both contained in a liposome.

2. The preparation according to claim 1, wherein the preparation is used for the prevention of type I diabetes.

3. The preparation according to claim 1, wherein the preparation is administered in the form of subcutaneous or intraperitoneal administration.

4. A method for prevention or treatment of type I diabetes, comprising administering a therapeutically or prophylactically effective amount of a preparation to a human in need of prevention or treatment of type I diabetes, wherein the preparation comprises (A) at least one member selected from the group consisting of insulin B chain, fragments thereof and variants thereof, and
(B) KRN7000, wherein the components (A) and (B) are both contained in a liposome.

5. The method for prevention or treatment according to claim 4, wherein the human is a human in need of the prevention of type I diabetes.

6. The method for prevention or treatment according to claim 4, wherein the preparation is administered in the form of subcutaneous or intraperitoneal administration.

7. The preparation according to claim 1, wherein the liposome further comprises diacylphosphatidylcholine.

8. The method for prevention or treatment according to claim 4, wherein the liposome further comprises diacylphosphatidylcholine.

* * * * *